(12) United States Patent
Bastian et al.

(10) Patent No.: US 7,074,916 B2
(45) Date of Patent: *Jul. 11, 2006

(54) PROCESS FOR THE SEPARATION OF DOUBLE-STRANDED/SINGLE-STRANDED NUCLEIC ACID STRUCTURES

(75) Inventors: Helge Bastian, Mettmann (DE); Simone Gauch, Haan (DE); Metin Colpan, Essen (DE); Petra Feuser, Cologne (DE)

(73) Assignee: QIAGEN GmbH, Hilden (DE)

( * ) Notice: Subject to any disclaimer, the term of this patent is extended or adjusted under 35 U.S.C. 154(b) by 548 days.

This patent is subject to a terminal disclaimer.

(21) Appl. No.: 10/340,834

(22) Filed: Jan. 13, 2003

(65) Prior Publication Data

US 2003/0224389 A1     Dec. 4, 2003

Related U.S. Application Data

(63) Continuation of application No. 09/613,311, filed on Jul. 10, 2000, now abandoned, which is a continuation of application No. 08/687,610, filed as application No. PCT/EP95/00445 on Feb. 8, 1995, now Pat. No. 6,180,778.

(30) Foreign Application Priority Data

Feb. 11, 1994 (DE) ............................... P 44 04 361

(51) Int. Cl.
C07H 21/04 (2006.01)
C12Q 1/68 (2006.01)
C12P 19/34 (2006.01)

(52) U.S. Cl. .......................... 536/25.4; 435/6; 435/91.2
(58) Field of Classification Search ............ 435/6
See application file for complete search history.

(56) References Cited

U.S. PATENT DOCUMENTS

| 5,075,430 A | 12/1991 | Little |
| 5,155,018 A | 10/1992 | Gillespie et al. |
| 5,314,809 A * | 5/1994 | Erlich et al. ............... 435/91.2 |
| 6,180,778 B1 * | 1/2001 | Bastian et al. ............. 536/25.4 |

FOREIGN PATENT DOCUMENTS

| EP | 0 325 032 A1 | 7/1989 |
| EP | 0 389 063 A2 | 9/1990 |
| EP | 0 580 305 A2 | 1/1994 |
| WO | WO 93/11221 | 6/1993 |

OTHER PUBLICATIONS

Egly et al., Journal of Chromatography, vol. 243, pp. 301-306 (1982).*

J.M. Egly et al., "Separation of Single-Stranded From Double-Stranded Nucleic Acids Using Acriflavin-Agarose Chromatography", Journal of Chromotography, 243, (1982), pp. 301-306.

* cited by examiner

*Primary Examiner*—Jeffrey Fredman
(74) *Attorney, Agent, or Firm*—Jacobsen Holman PLLC

(57) ABSTRACT

The present invention pertains to a process for the chromatographic separation of nucleic acid mixtures into their double-stranded and single-stranded nucleic acid fractions by simultaneously absorbing said nucleic acids as a whole to a mineral support, followed by separation into double-stranded and single-stranded nucleic acids by fractional elution, or by selectively absorbing double-stranded or single-stranded nucleic acid of a liquid sample to a mineral support, as well as solutions and a kit for performing the process according to the invention.

30 Claims, 2 Drawing Sheets

R 1 2 3 4 5 6 7 8 9

R 10 11 12 13 14 15 16 17 18

R 1 2 3 4 5 6 7 8 9

R 10 11 12 13 14 15 16 17 18

PROCESS FOR THE SEPARATION OF DOUBLE-STRANDED/SINGLE-STRANDED NUCLEIC ACID STRUCTURES

This is a continuation of application Ser. No. 09/613,311 filed Jul. 10, 2000 now abandoned, which is a continuation of Ser. No. 08/687,610 filed Aug. 8, 1996 now U.S. Pat. No. 6,180,776, which is a 371 of PCT/EP95/00445, filed Feb. 8, 1995.

The present invention pertains to a process for the chromatographic separation of nucleic acid mixtures into their double-stranded and single-stranded nucleic acid fractions by simultaneously absorbing whole nucleic acids to a mineral support, followed by separation into double-stranded nucleic acid and single-stranded nucleic acid by fractional elution, or by selectively absorbing double-stranded nucleic acid or single-stranded nucleic acid of a liquid sample to a mineral support, as well as solutions and a kit for performing the process according to the invention.

The preparation of nucleic acids, both RNA and DNA, has increasingly gained importance. This involves, for example, lysing the biological sources from which the RNA or DNA is to be isolated, for instance, by mechanical action or chemical action, such as treatment with detergents etc. Thus, the cell lysis for recovery of the nucleic acid is usually followed by a cesium chloride density gradient centrifugation or an extraction with phenol. Although useful for the isolation of nucleic acids, these methods have drawbacks which make their use difficult. Thus, cesium chloride density gradient centrifugation requires the use of time-consuming and expensive ultracentrifugation while working with phenol is questionable for workers' protection reasons.

Thus, attempts to simplify the isolation of nucleic acids have been abundant in the past.

DE 36 39 949 A1, DE 40 34 036 A1 or DE 41 39 664 A1 are concerned, e.g., with improvements of nucleic acid purification by chromatographic methods while avoiding methods which require much equipment, such as high pressure liquid chromatography (HPLC). Although these methods already represent a progress over, for example, ultracentrifugation or phenol extraction, they are relatively complicated technically and labor-intensive. Since a number of successive purification steps is frequently required for fractionation, processing of small sample quantities is particularly problematic, e.g., due to substance losses.

EP 0 389 063 A2 also pertains to a process for the isolation of nucleic acids. The source containing the nucleic acids is lysed in the presence of chaotropic ions and then treated with a material which will adsorb nucleic acids under such conditions. As such materials, there are mentioned diatomaceous earth or other silica-containing mineral supports. It is possible according to the method mentioned in EP 0 389 063 A2 to simultaneously isolate RNA and DNA, and RNA and ssRNA. A desirable fractionation of the nucleic acids bound to the silicon dioxide support into DNA and RNA fractions is not achieved, however. RNA can then be digested by the addition of RNase, leaving the DNA.

In U.S. Pat. No. 5,155,018, Gillespie et al. disclose a process for the isolation and purification of biologically active RNA from biological sources containing RNA, DNA and other cell contents. The source containing RNA is contacted with particles which consist of silica gel containing materials, such as finely divided glass. The binding buffer from which the RNA is adsorbed to the material is acidified solutions containing chaotropic salts. Under such conditions, RNA is bound to the silica material while DNA is not. The use of acidified chaotropic buffers has the drawback that an acidification of binding buffers containing guanidinium thiocyanate (GTC) involves the risk of hydrogen cyanide formation, and thus particular precautions must be taken. Also, the DNA is destroyed by the action of acid. In addition, DNA purification from the authentic sample cannot be performed by this method.

In U.S. Pat. No. 5,075,430, Little describes a process for the purification of plasmid and other DNA, both single-stranded and double-stranded, by immobilizing the DNA on diatomaceous earth in the presence of a chaotropic agent, followed by elution of the DNA with water or a buffer of low salt content. Purification of DNA/RNA is not possible according to this method.

In "Analytical Biochemistry" 121, pages 382 to 387 (1982), M. A. Marko et al. describe a process for the isolation of highly purified plasmid DNA on a large scale using alkaline extraction and binding to glass powder. A fractionation and separate purification of RNA and DNA from a single sample is not described.

The raw preparation of the nucleic acids is followed by subsequent reactions. These subsequent reactions make certain demands on both the isolation procedure and the purity and integrity of the isolated nucleic acids. Especially when followed by enzymatic amplification reactions, such as PCR (polymerase chain reaction), LCR (ligase chain reaction), NASBA (nucleic acid sequence-based amplification), or 3SR (self-sustained sequence replication), the preparation of the nucleic acids should be possible without the risk of cross-contaminations by other samples, and the isolated nucleic acids should be free of interfering cell components and/or metabolites. Due to its specificity and sensitivity, enzymatic amplification of DNA (e.g. PCR) or RNA (e.g. RNA-PCR) is gaining importance, not only in basic research, but also increasingly in the medical field for diagnostic use, such as, for example, for the detection of nucleic acid sequences from minute amounts of cells and/or tissues or biopsy materials, or for the detection of viral nucleic acids from blood or plasma. In addition to the requirements mentioned, these applications make the highest demands on yields and reproducibility of the process for the isolation of nucleic acids.

One object of the invention is to provide a process which is successful not only in separately purifying RNA and DNA from the same biological sample, such as cell lysates and tissue lysates, but generally in separating double-stranded from single-stranded nucleic acids. Operation of the process should be as inexpensive as possible, for example, by using inexpensive unmodified separating materials. In addition, the process should also be suited for sample preparation for diagnostics and be compatible with various amplification methods. Further, the drawbacks mentioned in the discussion of the prior art should be avoided.

Surprisingly, the object of the invention is achieved by a process having the features of claim 1 in its process alternatives 1.1 to 1.4. Subclaims 2 to 11 pertain to preferred embodiments of the process according to the invention, claims 12 to 21 pertain to solutions for use in the process according to the invention or the use of such solutions, and claim 22 pertains to a kit containing the components necessary for performing the process according to the invention.

In more detail, the process according to the invention for the fractionation of double-stranded and single-stranded nucleic acid structures from biological sources is represented by the following process alternatives.

Figure 1:
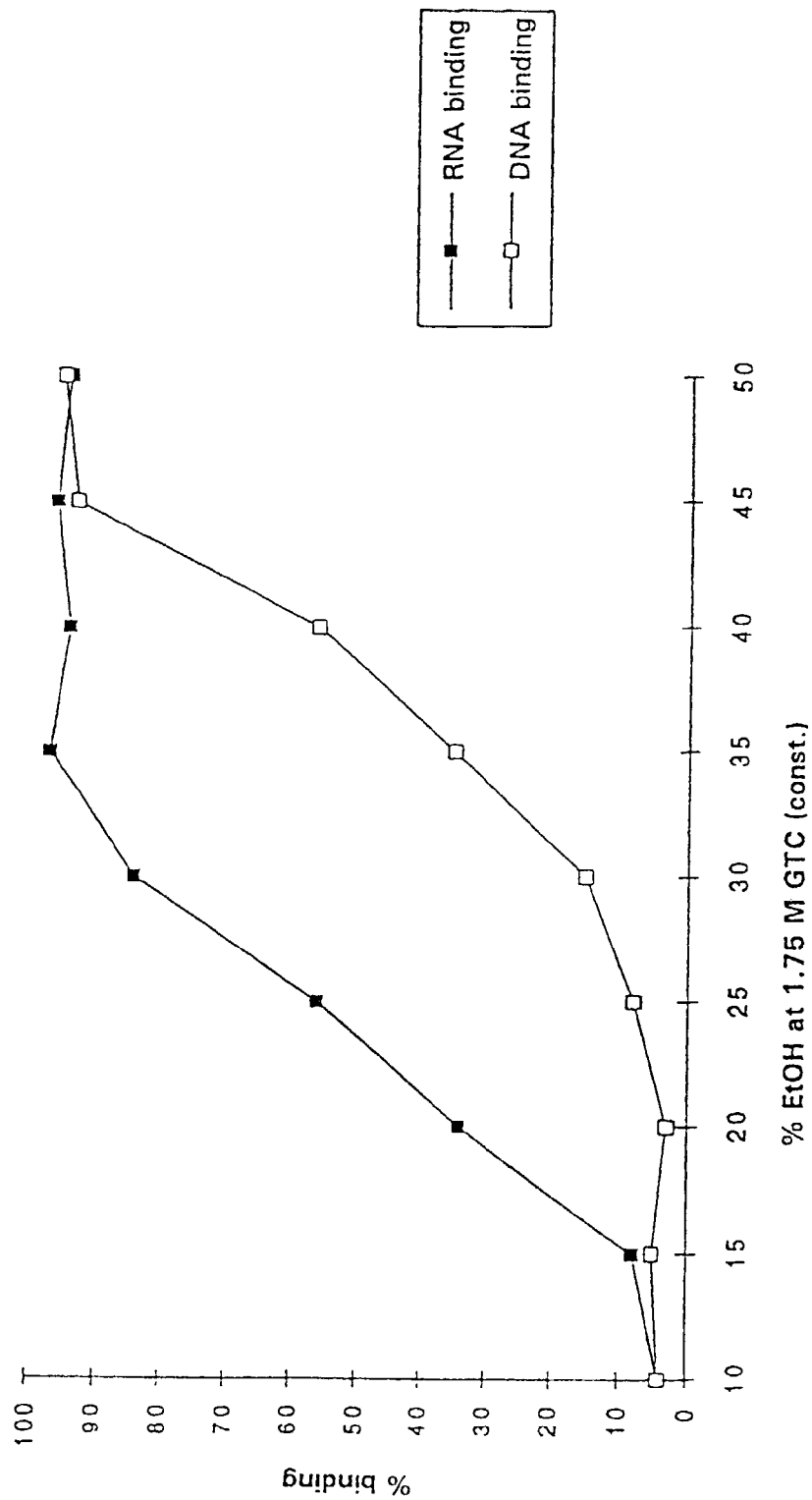
FIG. 1 graphically shows the binding of single-standed/double-stranded nucleic acid exemplified by single-stranded RNA and double-stranded DNA.

The sample containing the nucleic acid types to be separated (single-stranded and double-stranded ones) is treated with at least one mineral support wherein the treatment conditions are adjusted with an appropriate aqueous mixture of salts, especially chaotropic substances, and materials containing alcohol groups, such that the single-stranded nucleic acid fraction is predominantly adsorbed on a first mineral support whereas the double-stranded nucleic acid is not adsorbed. Then, the double-stranded nucleic acid flowing out can be further processed with per se known methods. After optionally performed washing steps, the single-stranded nucleic acid adsorbed on the first mineral support is eluted under conditions of low ionic strength or with water. The non-adsorbed double-stranded nucleic acid collected can be further purified, e.g., by subsequently adjusting the fraction with an appropriate aqueous mixture of salts, especially chaotropic substances, and materials containing alcohol groups to such conditions that the double-stranded nucleic acid becomes adsorbable to a second mineral support and, after optionally performed washing steps, becomes elutable under conditions of low ionic strength or with water.

In a second embodiment of the process according to the invention, the treatment conditions for the separation of single-stranded nucleic acid and double-stranded nucleic acid are adjusted such that materials complexing alkaline earth metal ions are contained in the solution in the absence of materials containing alcohol groups wherein said single-stranded nucleic acid is not adsorbed on the first mineral support and can be separated from the rest of the sample. The single-stranded nucleic acid separated can then be further processed by per se known methods. The double-stranded nucleic acid, however, predominantly binds to the first mineral support and, after optionally performed washing steps, can be eluted under conditions of low ionic strength or with water. The double-stranded nucleic acid thus obtained can then be further purified by per se known methods.

The non-adsorbed single-stranded nucleic acid collected can subsequently be adjusted, in particular by addition of materials containing alcohol groups, to such conditions that the single-stranded nucleic acid becomes adsorbable to a second mineral support and, after optionally performed washing steps, becomes elutable under conditions of low ionic strength or with water.

If the treatment conditions are adjusted such that wetting, washing or dispersing agents are contained in the solution in the absence of materials containing alcohol groups, the single-stranded nucleic acid is not adsorbed on a first mineral support under such conditions and thus can be separated from the rest of the sample and further processed. The double-stranded nucleic acid, however, predominantly binds to the first mineral support and, after optionally performed washing steps, can be eluted under conditions of low ionic strength or with water. The eluted double-stranded nucleic acid can then be further processed by per se known methods.

The non-adsorbed single-stranded nucleic acid collected can subsequently be adjusted, preferably by addition of materials containing alcohol groups, to such conditions that the single-stranded nucleic acid becomes adsorbable to a second mineral support and, after optionally performed washing steps, becomes elutable under conditions of low ionic strength or with water.

Another embodiment of the process according to the invention ensures the fractionation of single-stranded nucleic acid and double-stranded nucleic acid bound in common. This involves adjusting the treatment conditions with an appropriate aqueous mixture of salts, especially chaotropic substances, and materials containing alcohol groups, such that the whole nucleic acid consisting of single-stranded nucleic acid and double-stranded nucleic acid becomes adsorbed on a mineral support, followed by fractionation of the double-stranded/single-stranded nucleic acid bound to the first support by selective elution of the double-stranded nucleic acid by treatment with a solution of reduced ionic strength and reduced concentration of a material containing alcohol groups, or elution of the single-stranded nucleic acid with a solution containing a material complexing alkaline earth metal ions and/or a wetting, washing or dispersing agent as well as one or more types of salts, especially chaotropic substances. In the first case, the single-stranded nucleic acid then remains bound to the support whereas in the second case the double-stranded nucleic acid remains bound to the mineral support. The respective eluted fraction can then be further processed by per se known methods.

Adjusting the treatment conditions with materials containing alcohol groups and salts, especially chaotropic substances, for the separation of the nucleic acids is performed, according to the invention, based on the following physicochemical principles which are formulated here for the first time.

FIG. 1 shows the binding of single-stranded/double-stranded nucleic acid exemplified by single-stranded RNA and double-stranded DNA. Described here is the RNA/DNA binding from a tissue lysate to a mineral support as a function of the concentration of a material containing alcohol groups (here, ethanol) and a chaotropic substance (here, GTC). Under the condition that the concentration of one of the substances, alcohol or chaotropic substance, is constant, it is found that at a high alcohol concentration and/or amount of chaotropic substance, both types of nucleic acid (RNA/DNA) are bound to the mineral support. If the concentration of one or both substances (alcohol or chaotropic agent) becomes less than a defined value, none of the nucleic acids will bind to the mineral support to any substantial extent. Surprisingly, in between, RNA and DNA will bind to the mineral support to such different extents as can be made use of for the separation of the nucleic acids. Thus, proceeding from cells, and after lysis of the cells with a high concentration of chaotropic substances, the concentrations of chaotropic substance and material containing alcohol groups can be adjusted by subsequent addition of a material containing alcohol groups or a mixture of material containing alcohol groups and water or buffer such that a selective binding of the RNA is achieved while the DNA remains in the breakthrough. In the example according to FIG. 1, concentrations of 1.75 M GTC and 30% by volume of ethanol would be selected in order to achieve a separation of RNA from DNA by fractional binding.

On the other hand, simultaneous binding of single-stranded nucleic acid and double-stranded nucleic acid to the mineral support can be achieved under conditions of high concentration of material containing alcohol groups and/or high concentration of chaotropic substance, and desorption of the double-stranded nucleic acid can be initiated first by reducing the concentration of the material containing alcohol groups and/or chaotropic substance. The single-stranded nucleic acid remains bound and will elute when the concentration of one or both of the substances is still reduced. In the example according to FIG. 1, concentrations of 1.75 M GTC and 45% by volume of ethanol would be selected in order to achieve binding of the whole nucleic acid. As illustrated in example 8, concentrations of 0.3 M GTC and 10% by volume of ethanol would be selected for selective desorption of the DNA.

Thus, it is possible to separate RNA and DNA by adsorption to a mineral support, or to adsorb the whole nucleic acid first to the mineral support and then to selectively elute the single-stranded nucleic acid or double-stranded nucleic acid.

Optionally, washing steps may also be performed prior to the elution of the respective nucleic acid (single-stranded nucleic acid or double-stranded nucleic acid).

Then, the elution will be effected respectively under conditions of low ionic strength or with water. The nucleic acid desorbed first from the mineral support is subsequently adjusted by increasing the ionic strength and/or concentration of the materials containing alcohol groups such that the double-stranded nucleic acid or single-stranded nucleic acid is adsorbed to a second mineral support and, after optionally performed washing steps, is eluted under conditions of low ionic strength or with water.

Since nucleic acids will adsorb to mineral supports, for example, in sodium chloride/ethanol mixtures as well and can be eluted under conditions of low ionic strength or with water, it may be supposed that the salt solutions used in the process according to the invention need not necessarily contain chaotropic salts, but that any salt solution in combination with a material containing alcohol groups may be used.

The process according to the invention advantageously enables the processing of small sample quantities, ensures a simple and safe handling and avoids precipitation steps. Further, the process according to the invention can be performed in a rather inexpensive and little personnel-intensive way and readily enables the simultaneous processing of numerous samples. Due to its versatility and easy handling, the process is also suited for automated operation.

By the process according to the invention, double-stranded/single-stranded nucleic acid structures can be separated from sources containing nucleic acid structures. The sources which can contain the nucleic acid structures to be separated may include, e.g., the sources mentioned in claim 7. These are, in particular, cell cultures, tissues of all kinds, body fluids, such as blood, plasma, serum, urine, faeces; microorganisms, such as bacteria, viruses, such as cytomegaly virus, HIV, hepatitis B, hepatitis C, hepatitis δ virus; plants, plant parts, embryos, germs, fruits, or mixtures containing nucleic acids following enzymatic reactions, such as in vitro transcription and/or cDNA synthesis and/or reverse transcription with subsequent polymerase chain reaction (PCR).

Preferably, cells are first lysed in an aqueous lysis system containing chaotropic substances and/or other salts by, in the simplest case, adding it to the cells. Optionally, the lysis process may be promoted by mechanical action.

Thereafter, the sample thus treated is further processed depending on the problem, i.e. which type of nucleic acid is to be separated from the other, as described in the process steps 1.1 to 1.4 according to claim 1.

Some of the starting materials mentioned cannot be lysed directly in aqueous systems containing chaotropic substances, such as bacteria, for instance, due to the condition of their cell walls. Therefore, these starting materials must be pretreated, for example, with lytic enzymes, prior to being used in the process according to the invention.

Systems for lysing the sources containing the nucleic acids are preferably solutions of chaotropic substances in concentrations of from 0.1 to 10 M. As said chaotropic substances, there may be used, in particular, salts, such as sodium perchlorate, guanidinium chloride, guanidinium isothiocyanate/guanidinium thiocyanate, sodium iodide, potassium iodide, and/or combinations thereof.

Aqueous solutions containing salts, such as sodium chloride, lithium chloride, potassium chloride, sodium acetate, magnesium chloride, in concentrations of from 0.1 to 10 M, or urea in corresponding concentrations of from 0.1 to 10 M, and/or combinations of such materials may also be used as aqueous systems for lysing or binding the sources containing the nucleic acids.

The materials containing the alcohol groups are preferably lower aliphatic alcohols having from 1 to 5 carbon atoms, such as methanol, ethanol, isopropanol, butanol and pentanol. They are preferably employed in concentrations of from 1 to 90% by volume.

The mineral support preferably consists of porous or non-porous metal oxides or mixed metal oxides, silica gel, materials predominantly consisting of glass, such as unmodified glass particles, powdered glass, quartz, alumina, zeolites, titanium dioxide, zirconium dioxide, the particle size of the mineral support material being from 0.1 μm to 1000 μm, and the pore size being from 2 to 1000 μm. Said porous or non-porous support material may be present in the form of loose packings or may be embodied in the form of filter layers made of glass, quartz or ceramics, and/or a membrane in which silica gel is arranged, and/or particles or fibers made of mineral supports and fabrics of quartz or glass wool, as well as latex particles with or without functional groups, or frit materials made of polyethylene, polypropylene, polyvinylidene fluoride, especially ultra high molecular weight polyethylene, high density polyethylene.

As the substance binding alkaline earth metal ions, there may be used, in particular, ethylenediaminetetraacetic acid (EDTA) or EGTA, and a sarcosinate may be employed as a wetting, washing or dispersing agent.

If desired, the nucleic acids obtained according to the invention may be further purified by chromatographic methods, such as anion exchange chromatography.

In the process according to the invention, RNA, in particular, as the single-stranded nucleic acid, may be separated from double-stranded nucleic acid (DNA). If DNA is present in a single-stranded form, such DNA may also be separated from double-stranded DNA, as well as from double-stranded RNA.

The solutions employed in the process according to the invention are also a subject-matter of the present invention. As the lysis buffers and/or binding buffers, there may be used according to the invention, in particular, aqueous solutions containing from 0.5 to 8.0 M of guanidinium isothiocyanate/guanidinium thiocyanate, and/or guanidinium chloride, and from 0 to 50% of ethanol and/or isopropanol.

As the solution for washing out or eluting nucleic acids bound to the mineral support, there may be used an aqueous solution containing from 0.1 to 3 M of guanidinium isothiocyanate/guanidinium thiocyanate, and/or guanidinium chloride, together with from 1 to 30% of ethanol and/or isopropanol.

As an aqueous solution system to be employed for binding double-stranded nucleic acid to mineral supports, there may be used an aqueous solution containing from 1 to 5 M of guanidinium isothiocyanate, and/or from 1 to 8 M of guanidinium chloride, together with from 0.1 to 5% of sarcosinates, or from 5 mM to 200 mM of EDTA For binding double-stranded nucleic acid, there may also be used a solution containing from 1 to 5 M of guanidinium thiocyanate, and/or from 1 to 8 M of guanidinium chloride, and from 5 mM to 200 mM of EDTA or EGTA.

The kit of components according to the invention for performing the process contains, in particular, hollow bodies suited for flow-through in which the mineral support or supports is (are) arranged in the form already described above. The mineral support may be present in loose packing, fixed between two means, or in the form of membranes which are arranged within the hollow body. In addition, the kit may contain solutions, or the components for formulating said solutions may be present in a concentrated form. The user will then be able to prepare the solutions respectively needed in the necessary concentrations.

Another advantageous component of the kit is a device for homogenizing the solution of cell lysates. A particularly preferred device for homogenizing is proposed in the International Patent Application WO 95/18851. This device essentially consists of at least two porous layers wherein said porous layers have decreasing pore sizes as seen in the direction of flow through the layers. When the cell lysate passes through the decreasing pore sizes, the viscous solutions of the cell lysate are being homogenized.

The invention will be illustrated in more detail by means of the following examples.

MATERIALS AND METHODS

1. Silica Support Materials
   Silica support materials were used in the form of membranes or suspended particles.
   1.1. Silica Membranes
   Two layers of a silica membrane (e.g., fiber glass filter of the firm of Whatman) were fixed in a centrifuge chromatographic column ("spin column") as described in P 43 21 904. For support materials in membrane form, the standard protocol "spin procedure" was followed (cf. 4.1).
   1.2. Silica Particles
   A number of different silica particles (e.g. of the firms of Merck, Darmstadt, Germany, and Sigma, St. Louis) were used as a 50% suspension in the respectively used lysis buffer (cf. 3.1). The average particle diameters were, depending on the material, from 0.5 to 50 µm. The standard protocol "batch procedure" was followed (cf. 4.2).

2. Sources Containing Nucleic Acids
   2.1. Tissues
   The tissues employed for the preparation were freezed in liquid nitrogen immediately after collected and stored at −70° C. Alternatively, fresh tissue may be used.
   2.2. Plants
   Leaves were ground in a mortar under liquid nitrogen to give a fine powder and directly employed for the preparation or stored at −70° C.
   2.3. Cell Culture
   After harvesting, cells were washed twice with PBS and pelletized. Aliquots containing an appropriate number of cells (determined by counting in a Thoma chamber) were freshly used for the preparation or stored at −20° C.
   Alternatively, adherently growing cells may be washed in the culture dish and lysed directly in the culture dish by addition of the respective lysis buffer (cf. 3.1).
   2.4. Plasma
   ACD blood was centrifuged at 3000×g for 10 min, the supernatant was removed and again centrifuged as above. Aliquots were made from the supernatant obtained after the second centrifugation and stored at −70° C.
   2.5. Bacteria
   Cultures were inoculated with an overnight culture and grown to an $OD_{600}$ of 0.5 to 0.8. Aliquots containing the appropriate number of cells (1 $OD_{600}$=$10^9$ cells/ml) were pelletized, and the cell pellets were stored at −20° C. or freshly used for the preparation.

3. Reagents
   3.1. Lysis Buffers
   L1 4.5 M GTC (guanidinium thiocyanate), 25 mM Na citrate, pH 7.5, 0.7% β-mercaptoethanol (MSH)
   L2 4.0 M GTC, 25 mM Na citrate, pH 7.5, 0.7% β-MSH
   L3 5.0 M GTC, 50 mM TRIS/HCl, pH 7.0
   L4 3.5 M GTC, 25 mM Na citrate, pH 7.5, 1% β-MSH
   L5 2.5 M GTC, 25 mM Na citrate, pH 7.5, 1% β-MSH, 30% ethanol
   L6 8.0 M GuHCl (guanidinium chloride), 20 mM MOPS, pH 7.0, 0.7% β-MSH
   L7 3.0 M GTC, 25 mM Na citrate, pH 7.5, 1% β-MSH
   L8 4.0 M GTC, 50 mM TRIS/HCl, pH 7.5, 1% sarcosyl
   L9 4.0 M GTC, 50 mM TRIS/HCl, pH 7.5, 25 mM EDTA
   3.2. Binding Reagent
   B1 ethanol
   B2 n-butanol
   B3 isopropanol
   B4 70%-ethanol in water
   B5 5.9 M GTC
   3.3. Washing Buffers
   W1 2.0 M GTC, 25 mM TRIS/HCl, pH 7.5, 30% ethanol
   W2 4.0 M GTC, 40 mM TRIS/HCl, pH 7.5, 20% isopropanol
   W3 1.0 M GTC, 25 mM TRIS/HCl, pH 7.5, 20% ethanol
   W4 5.0 M GuHCl, 15 mM MOPS, pH 7.0, 37% ethanol
   W5 0.5 M GTC, 25 mM TRIS/HCl, pH 7.5, 10% ethanol 4. Standard Protocols
   4.1. "Spin Procedure"
   1) Add lysis buffer (cf. 3.1.) to the source containing nucleic acid and homogenize completely by means of a hand homogenizer.
   2) Add binding reagent (cf. 3.2.) to adjust the respective binding conditions.
   3) Pipette the lysate onto the spin column and centrifuge through the membrane of the spin column in a table-top centrifuge at 10,000 rpm for 15 s; if the volume of the lysate exceeds the fill volume of the spin column, repeat this binding step.
   4) Either process further, if desired, or discard the column break-through.
   5) Pipette 700 µl of washing buffer (cf. 3.3.) onto the spin column and centrifuge as described in 3) to remove contaminating cell components.
   6) Wash the membrane-bound nucleic acids twice with 700 µl of 80% ethanol in water to become salt-free, proceeding as in 5).
   7) Centrifuge the spin column at maximum number of revolutions for two minutes to remove ethanol completely.

8) Pipette 50 to 100 µl of water heated at 80° C. directly onto the membrane of the spin column and centrifuge at maximum number of revolutions for 1 minute to elute the nucleic acids; if necessary, repeat the elution step.

4.2. "Batch Procedure"

1) Add lysis buffer (cf. 3.1.) to the source containing nucleic acid and homogenize completely by means of a hand homogenizer.
2) Add binding reagent (cf. 3.2.) to adjust the respective binding conditions.
3) Add 50 µl of silica suspension (50% in lysis buffer) and incubate at room temperature for 10 minutes for the nucleic acids to bind, with repeated vortexing.
4) Centrifuge in a table-top centrifuge at 10,000 rpm for 15 seconds to pelletize the silica material.
5) Pipette off and process further, if desired, or discard the supernatant.
6) Add 700 µl of washing buffer (cf. 3.3.) to the pellet, vortex, until the pellet is completely resuspended, and centrifuge as in 4).
7) Repeat washing step 6) twice with 700 µl of 80% ethanol in water to wash the silica material salt-free.
8) Dry the pelletized silica material at 56° C. for 10 minutes with the lid open.
9) Add 50 to 100 µl of water, resuspend the pellet completely by vortexing and incubate at 56° C. for 10 minutes, with repeated vortexing; if necessary, repeat this elution step.
10) Centrifuge at maximum number of revolutions for 1 minute and transfer the supernatant to a new reaction vessel.

5. Electrophoretic Methods

The isolated nucleic acids were analyzed on agarose gels stained with ethidium bromide. To this purpose, 1.2% formaldehyde or 1.2% 1×TBE gels were prepared.

After the run, formaldehyde gels were agitated in water for 3 to 4 hours, then in 10 µg/ml RNase A over night, to digest the RNA and thus render the DNA more readily visible. TBE gels were RNase-digested without prior equilibrating.

The examples described in the following will illustrate the performance of the process according to the invention. All nucleic acids accordingly isolated were electrophoretically analyzed and quantified by photometry. The $OD_{260/280}$ value was between 1.7 and 2.0 for all eluates.

REFERENCE EXAMPLES 1 TO 5

Isolation of Whole Nucleic Acid

In the following reference examples 1 to 5, the binding, washing and elution conditions were respectively selected such that both DNA and RNA would bind to the mineral support and be eluted together.

These examples will illustrate the use of a number of different alcohols (ethanol, isopropanol, butanol) as binding reagents.

Reference Example 1

Isolation of Whole Nucleic Acid from Kidney Tissue

From 15 mg of kidney tissue (rat), whole nucleic acid was isolated according to standard protocol 4.1. The tissue was mixed with 400 µl of L1 and homogenized, followed by addition of 280 µl of B1. The first washing step was performed with W1, and the elution volume was 2×50 µl.

Reference Example 2

Isolation of Whole Nucleic Acid from Liver Tissue

From 7 mg of liver tissue (rat), whole nucleic acid was isolated according to standard protocol 4.1. The tissue was mixed with 300 µl of L2 and homogenized, followed by addition of 200 µl of B2. The first washing step was performed with W1, and the elution volume was 2×50 µl.

Reference Example 3

Isolation of Whole Nucleic Acid from HeLa Cells

From $1\times10^6$ HeLa cells, whole nucleic acid was isolated according to standard protocol 4.1. The cells were mixed with 400 µl of L2 and homogenized, followed by addition of 200 µl of B1. The first washing step was performed with W1, and the elution volume was 1×50 µl.

Reference Example 4

Isolation of Whole Nucleic Acid from Plasma

Whole nucleic acid from plasma was isolated in two parallel runs according to standard protocols 4.1 and 4.2, respectively. In each case, 800 µl of L3 and 660 µl of B2 were added to 200 µl of plasma and mixed; homogenization was not necessary here. To the mixture for the "batch procedure" (4.2), there was additionally added 40 µl of silica suspension. In both runs, the first washing step was performed with W2, and the elution volume was 2×100 µl.

Example 1

Fractional Binding of RNA and DNA at Constant GTC Concentration and with Increasing Ethanol Concentration The dependence of RNA/DNA binding to the mineral support at constant GTC concentration and with increasing ethanol concentration was demonstrated by lysing 10 mg of a kidney tissue in 350 µl of L4 for each sample run and adding 350 µl of an ethanol/water mixture for each run to adjust the ethanol concentration, the ethanol content of this mixture being between 20 and 90% ethanol in water. To another batch, 350 µl of absolute ethanol was added. In the respective runs, this corresponded to binding conditions of a constant GTC concentration of 1.75 M and an increasing ethanol concentration in the range of from 10 to 50% (cf. FIG. 1).

In a first series of experiments, 150,000 cpm of a $^{32}P$-labeled 0.9 kb in vitro transcript were given to each of the lysates thus adjusted, and the lysates were pipetted onto the mineral support fixed in a spin column. Centrifugation was performed in a table-top centrifuge at 10,000 rpm for 15 seconds, and the amount of radioactivity bound to the column and present in the column break-through was measured by Cherenkov counting.

The series of experiments was repeated wherein 150,000 cpm of a linearized pTZ plasmid, $^{32}P$-labeled by a Klenow filling reaction, was added instead of the $^{32}P$-labeled RNA.

As shown in FIG. 1, the RNA fraction will bind to the mineral support under the conditions described already from ethanol concentrations of greater than 25% whereas the DNA fraction will bind only from ethanol concentrations of greater than 40%.

Examples 2 to 8

Isolation of Whole RNA

In the following examples, the alcohol/salt mixtures for binding to the mineral support were selected such (cf. FIG. 1) that a selective RNA binding was achieved.

The binding conditions were respectively adjusted to the type of lysed material (tissue, cell culture, plants, bacteria)

The examples illustrate the use of GTC, GuHCl or GTC/ethanol mixtures for the lysis of the starting materials. The integrity of the isolated RNA was verified by Northern Blotting or RT-PCR.

In these examples, the DNA not bound to the support was not further processed. The further purification of DNA from the column break-through will be shown in example 12. In addition, the DNA may be further purified by adjusting the binding conditions to those chosen in reference examples 1 to 5.

Example 2

Isolation of Whole RNA from Spleen Tissue

From 15 mg of spleen tissue (mouse), whole RNA was isolated according to standard protocol 4.1. The tissue was mixed with 350 µl of L4 and homogenized, followed by addition of 350 µl of B4. The first washing step was performed with W3, and the elution volume was 1×50 µl.

Example 3

Isolation of Whole RNA from Liver Tissue (A)

In this example, an ethanol-containing lysis buffer was used so that standard protocol 4.1 was slightly modified.

Eight milligrams of liver tissue (rat) was mixed with 700 µl of L5 and homogenized. The lysate was pipetted onto the spin column and standard protocol 4.1 performed from step 3). The first washing step was performed with W3, and the elution volume was 1×50 µl.

Example 4

Isolation of Whole RNA from Liver Tissue (B)

From 15 mg of liver tissue (rat), whole RNA was isolated according to standard protocol 4.1. The tissue was mixed with 300 µl of L6 and homogenized, followed by addition of 175 µl of B1. The first washing step was performed with W4, and the elution volume was 1×50 µl.

Example 5

Isolation of Whole RNA from HeLa Cells

From $1 \times 10^7$ HeLa cells, whole RNA was isolated in two parallel runs according to standard protocols 4.1 and 4.2, respectively. In each case, the cells were mixed with 350 µl of L7 and homogenized, followed by addition of 350 µl of B4. To the mixture for the "batch procedure" (4.2), there was additionally added 50 µl of silica suspension. The first washing step was performed with W3, and the elution volume was 1×50 µl.

Example 6

Isolation of Whole RNA from Tobacco

For the isolation of whole RNA from plants, standard protocol 4.1 is slightly modified. After step 1) of the protocol (lysis), a centrifugation step at 5000 rpm in a table-top centrifuge is inserted to separate off unlysed cell components, such as fiber residues. The supernatant is removed, mixed with binding reagent and further processed according to the standard procedure from step 2).

From 100 mg of tobacco leaves, whole RNA was isolated according to standard protocol 4.1 as modified for plants. The powderized cell material was mixed with 600 µl of L2 and homogenized, followed by addition of 350 µl of B4. The first washing step was performed with W3, and the elution volume was 1×50 µl.

Example 7

Isolation of Whole RNA from *E. coli*

For the isolation of whole RNA from bacteria, an additional step is inserted before performing the standard protocol in order to lyse the cell walls of the bacteria. The cell pellet is resuspended in 400 µg/ml lysozyme in TE and incubated on ice for 5 min and at room temperature for 10 min. This is followed by lysing according to the standard procedure.

From $1 \times 10^9$ *E. coli* cells, whole RNA was isolated according to standard protocol 4.1 as modified for bacteria. The pellet was resuspended in 80 µl of 400 µl/ml lysozyme in TE and incubated as described above. This was followed by addition of 270 µl of L2, homogenization, and addition of 350 µl of B4. The first washing step was performed with W3, and the elution volume was 2×50 µl.

Example 8

Selective RNA Binding by Optimizing the Washing Buffer

As shown in this example, DNA contaminations can be removed from the specifically bound RNA by optimizing the washing buffer used in the first washing step (standard protocol 4.1.5).

According to standard protocol 4.1, $1 \times 10^6$ HeLa cells were lysed in 350 µl of L4 in each case, mixed with 350 µl of B4, and bound to the silica support. Then, the samples were washed with the following washing buffers in the first washing step:

TABLE 1

Washing buffer compositions for washing out DNA contaminations

| | washing buffer | | |
|---|---|---|---|
| sample no. | M GTC | 25 mM TRIS/HCl, pH 7.5 | % ethanol |
| 1 | 0.3 | + | 5 |
| 2 | 0.6 | + | 5 |

TABLE 1-continued

Washing buffer compositions for washing out DNA contaminations

| | | washing buffer | |
|---|---|---|---|
| sample no. | M GTC | 25 mM TRIS/HCl, pH 7.5 | % ethanol |
| 3 | 0.9 | + | 5 |
| 4 | 0.3 | − | 5 |
| 5 | 0.6 | − | 5 |
| 6 | 0.9 | − | 5 |
| 7–12 | as in 1–6, but 10% EtOH | | |
| 8–18 | as in 1–6, but 20% EtOH | | |
| R*) | 1.75 | − | 35 |

*)This sample served as a reference; the washing buffer composition corresponded to the binding conditions.

The further steps were performed according to the standard protocol; the elution volume was 1×50 µl.

Figure 2:
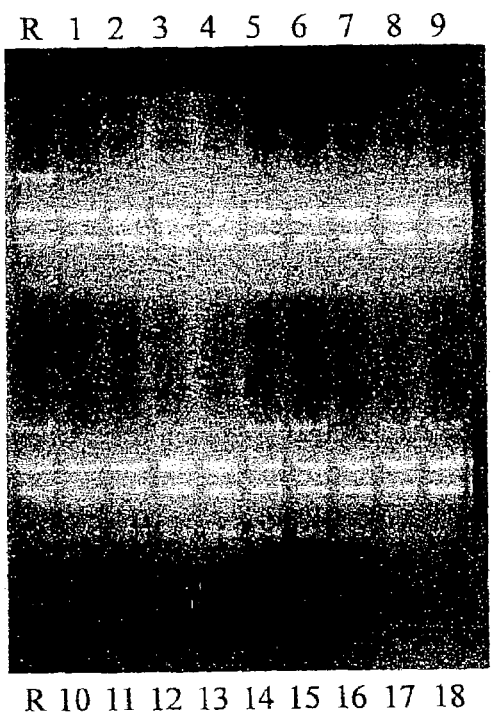
FIG. 2 is a photograph showing binding of nucleic acids applied to a formaldehyde gel following electrophoresis according to Example 8.

One half of the eluate was analyzed on a 1.2% formaldehyde gel (cf. FIG. 2). The gel was subsequently treated with RNase A as described under "electrophoretic methods" (cf. FIG. 3).

Figure 3:
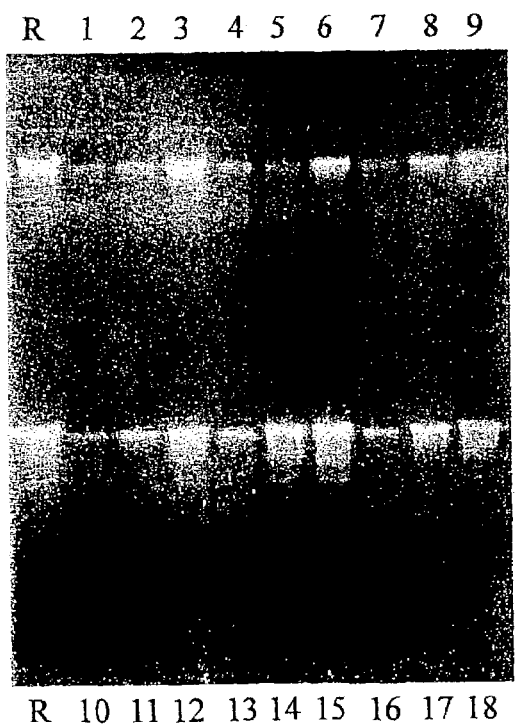
FIG. 3 is a photograph of the gel of FIG. 2 following treatment with RNase A.

Captions FIGS. 2 and 3

FIG. 2: 1.2% formaldehyde gel for analyzing the eluates from example 8, binding conditions: 1.75 M GTC, 12.5 min; Na citrate, pH 7.5, 35% ethanol; washing conditions: cf. Table 1. The designation of the tracks corresponds to the designation of the samples in Table 1.

FIG. 3: RNase digest of the gel of FIG. 2.

Examples 9 and 10

Isolation of DNA

In the following examples 9 and 10, the binding conditions were selected such that only DNA can bind to the mineral support whereas RNA will break through.

In these examples, the RNA not bound to the support was not further processed. The further purification of RNA from the column break-through will be shown in example 11. In addition, the RNA in the column break-through may be further purified by adjusting the binding conditions to those chosen in examples 2 to 8.

The selective DNA binding is performed in the lysis buffer in the absence of alcohol, i.e. step 2) of standard protocols 4.1 and 4.2 is omitted.

Example 9

Isolation of Genomic DNA from Kidney Tissue

Ten milligrams of kidney tissue (rat) was lysed in 700 µl of L8. The DNA was bound to the mineral support without addition of binding reagent and washed with 700 µl of L8 in the first washing step. Then, standard protocol 4.1 was performed from step 6). The elution volume was 2×50 µl.

Example 10

Isolation of Genomic DNA from HeLa Cells

1×10⁷ HeLa cells were lysed in 700 µl of L9. The DNA was bound to the mineral support without addition of binding reagent and washed with 700 µl of L9 in the first washing step. Then, standard protocol 4.1 was performed from step 6). The elution volume was 2×50 µl.

Examples 11 to 13

Separation of Whole RNA and Genomic DNA

The following examples 11 to 13 for the separated processing of RNA and DNA from the same cell lysate are combinations of the above examples for RNA, DNA or whole nucleic acid isolations.

Separation can be performed by either differential binding or fractional elution of RNA and DNA.

Examples 11 and 12

Separation of Whole RNA and Genomic DNA by Differential Binding

For differential binding, there are again two possibilities:

After the lysis, the conditions may be selected either such that DNA will first bind to the mineral support (example 11), or else RNA may be adsorbed in the first binding step while DNA is further processed from the break-through (example 12).

Example 11

Isolation of Genomic DNA and Whole RNA from Kidney Tissue

Ten milligrams of kidney tissue (rat) was lysed in 350 µl of L8, and the DNA was bound to the mineral support in the lysis buffer. To the column break-through, there was added 350 µl of B4, and the whole RNA isolated in accordance with example 3.1. Isolation of the genomic DNA was performed as in reference example 1.

Example 12

Isolation of Whole RNA and Genomic DNA from Lung Tissue

From 20 mg of lung tissue (rat), the whole RNA was isolated as described in example 2. The not bound genomic DNA in the column break-through was isolated by adding 350 µl of B1 and 350 µl of B5 and binding the DNA to the mineral support as described in standard protocol 4.1 The first washing step was performed with W1, and the elution volume was 2×50 µl.

Example 13

Separation of Whole RNA and Genomic DNA by Fractional Elution

The following example illustrates the selective elution of the DNA fraction of the whole nucleic acid bound to the mineral support.

The binding conditions are selected such that the whole nucleic acid will bind to the mineral support. The DNA fraction is subsequently eluted while the RNA fraction remains bound. The eluted DNA is bound to another mineral support by readjusting to DNA binding conditions (cf. FIG. 1) and further processed.

Isolation of Genomic DNA and Whole RNA from Liver Tissue

Fifteen mg of liver tissue (swine) were lysed in 300 μl of L2 according to standard protocol 4.1, 1) to 4), mixed with 250 μl of B1, and the whole nucleic acid bound to the mineral support. The DNA fraction was eluted with 300 μl of W5, while the support material with the still bound RNA fraction was treated according to standard protocol 4.1 from 5). The DNA fraction was isolated from the eluate by addition of 350 μl of B1 and 250 μl of B5 and binding to another mineral support according to standard protocol 4.1.

The invention claimed is:

1. In a medical diagnostic process including the amplification of nucleic acids, the improvement comprising making use of a process for the separation of single-stranded nucleic acids from double-stranded nucleic acids by treatment of a biological source, thereof, said treatment comprising the steps of:
    a) applying to a first mineral support an aqueous solution containing a sample of said source under conditions whereby said first mineral support adsorbs only one of said single- or double-stranded nucleic acids followed by, optionally, washing said first mineral support; and
    b) applying to a second mineral support the other of said single- or double-stranded nucleic acids, which was not adsorbed by the first mineral support, in an aqueous solution containing materials with alcohol groups.

2. The medical diagnostic process of claim 1 wherein
    i) the applying step to the first mineral support comprises adding to said aqueous solution salts and materials carrying alcohol groups in amounts such that the single-stranded, but not the double stranded, nucleic acids are adsorbed on the first mineral support, followed by, optionally, washing said first mineral support,
    ii) the double-stranded nucleic acids, which were not adsorbed on the first mineral support, are applied to the second mineral support in the presence of materials with alcohol groups in amounts such that the double-stranded nucleic acids are adsorbed on the second mineral support, followed by, optionally, washing said second mineral support, and
    iii) the single-stranded and double-stranded nucleic acids are eluted from the first and second mineral supports.

3. The medical diagnostic process of claim 1, wherein
    i) the applying step to the first mineral support comprises adding said aqueous solution with materials which complex alkaline-earth metal ions, in the absence of materials with alcohol groups, such that double-stranded, but not single-stranded nucleic acids are absorbed on the first mineral support,
    ii) the single-stranded nucleic acids, which were not absorbed on the first mineral support, are applied to the second mineral support in the presence of materials with alcohol groups in amounts such that the single-stranded nucleic acids are absorbed on the second mineral support, followed by optionally, washing said second mineral support, and
    iii) the double-stranded and single-stranded nucleic acids are eluted from the first and second mineral supports.

4. The medical diagnostic process of claim 1 wherein
    i) the applying step to the first mineral support comprises adding to said aqueous solution wetting, washing, or dispersing agents, in the absence of materials with alcohol groups, such that said double-stranded nucleic acids are absorbed on the first mineral support, followed by, washing said first mineral support,
    ii) the single-stranded nucleic acids, which were not absorbed on the first mineral support, are applied to the second mineral support in the presence of materials with alcohol groups in amounts such that the single-stranded nucleic acids are absorbed on the second mineral support, followed by optionally, washing said second mineral support, and
    iii) eluting the single-stranded and double-stranded nucleic acids from the first and second mineral supports.

5. The medical diagnostic process of claim 1 wherein
    a) the applying step to the first mineral support comprises adding to said aqueous solution salts and materials with alcohol groups in amounts such that both the single-stranded and double-stranded nucleic acids are adsorbed on the first mineral support,
    b) one of the single- or double-stranded nucleic acids is, selectively, first eluted from the first mineral support, followed by eluting the other of the single- or double-stranded nucleic acids, and
    c) the one of the single- or double-stranded nucleic acids, which was first eluted from the first mineral support, is applied to the second mineral support under conditions whereby the nucleic acids first eluted from the first mineral support are adsorbed on the second mineral support, followed by eluting the nucleic acids from the second mineral support.

6. The medical diagnostic process according to claim 1, further comprising the step, whereby, prior to applying the sample to the first mineral support, cells in said source containing the nucleic acids are lysed with chaotropic substances present in concentrations of from 0.1 to 10 M.

7. The medical diagnostic process according to claim 2, wherein the salts in said aqueous solution, applied to the first mineral support, are selected from the group consisting of sodium perchlorate, guanidinium chloride, guanidinium isothiocyanate/guanidinium thiocyanate, sodium iodide, potassium iodide, and combinations thereof, in concentrations of from 0.1 to 10 M.

8. The medical diagnostic process according to claim 3, wherein the salts in said aqueous solution, applied to the first mineral support, are selected from the group consisting of sodium perchiorate, guanidinium chloride, guanidinium isothiocyanate/guanidinium thiocyanate, sodium iodide, potassium iodide, and combinations thereof, in concentrations of from 0.1 to 10 M.

9. The medical diagnostic process according to claim 4, wherein the salts in said aqueous solution, applied to the first mineral support, are selected from the group consisting of sodium perchlorate, guanidinium chloride, guanidinium isothiocyanate/guanidinium thiocyanate, sodium iodide, potassium iodide, and combinations thereof, in concentrations of from 0.1 to 10 M.

10. The medical diagnostic process according to claim 5, wherein the salts in said aqueous solution, applied to the first mineral support, are selected from the group consisting of sodium perchlorate, guanidinium chloride, guanidinium isothiocyanatelguanidinium thiocyanate, sodium iodide, potassium iodide, and combinations thereof, in concentrations of from 0.1 to 10 M.

11. The medical diagnostic process according to claim 2, wherein the salts in said aqueous solution, applied to the first mineral support, are selected from the group consisting of sodium chloride, lithium chloride, potassium chloride, sodium acetate, magnesium chloride, urea, and combinations thereof, in concentrations of from 0.1 to 10 M.

12. The medical diagnostic process according to claim 3, wherein the salts in said aqueous solution, applied to the first mineral support, are selected from the group consisting of sodium chloride, lithium chloride, potassium chloride, sodium acetate, magnesium chloride, urea, and combinations thereof, in concentrations of from 0.1 to 10 M.

13. The medical diagnostic process according to claim 4, wherein the salts in said aqueous solution, applied to the first mineral support, are selected from the group consisting of sodium chloride, lithium chloride, potassium chloride, sodium acetate, magnesium chloride, urea, and combinations thereof, in concentrations of from 0.1 to 10 M.

14. The medical diagnostic process according to claim 5, wherein the salts in said aqueous solution, applied to the first mineral support, are selected from the group consisting of sodium chloride, lithium chloride, potassium chloride, sodium acetate, magnesium chloride, urea, and combinations thereof, in concentrations of from 0.1 to 10 M.

15. The medical diagnostic process according to claim 2, wherein said materials containing alcohol groups are lower aliphatic alcohols in concentrations of from 1 to 90% by volume, and said salts, are present in concentrations of from 1 to 10 M.

16. The medical diagnostic process according to claim 3, wherein said materials containing alcohol groups are lower aliphatic alcohols in concentrations of from 1 to 90% by volume, and said salts are present in concentrations of from 1 to 10 M.

17. The medical diagnostic process according to claim 4, wherein said materials containing alcohol groups are lower aliphatic alcohols in concentrations of from 1 to 90% by volume, and said salts, are present in concentrations of from 1 to 10 M.

18. The medical diagnostic process according to claim 5, wherein said materials containing alcohol groups are lower aliphatic alcohols in concentrations of from 1 to 90% by volume, and said salts, are present in concentrations of from 1 to 10 M.

19. The medical diagnostic process according to claim 1, wherein said first and second mineral supports are porous or non-porous and comprised of metal oxides or mixed metal oxides, silica gel, glass particles, powdered glass, quartz, alumina, zeolite, titanium dioxide, or zirconium dioxide, the particle size of the mineral supports is from 0.1 µm to 1000 µm, and the pore size of porous mineral supports is from 2 to 1000 µm.

20. The medical diagnostic process according to claim 1, wherein said biological source is selected from cell cultures, microorganisms, plants, or biological samples containing nucleic acids which are mixtures obtained from enzymatic reactions.

21. The medical diagnostic process according to claim 1, wherein the single- or double-stranded nucleic acids obtained, thereby are respectively purified by chromatographic steps.

22. The medical diagnostic process according to claim 3, wherein the complexes comprise alkaline earth metal ions bound to ethylenediaminetetraacetic acid (EDTA) or EGTA.

23. The medical diagnostic process of claim 4 wherein said wetting, washing or dispersing agent is a sarcosinate.

24. The medical diagnostic process according to claim 1, wherein said single-stranded nucleic acid is RNA and said double-stranded nucleic acid is DNA.

25. The medical diagnostic process according to claim 2, wherein said single-stranded nucleic acid is RNA and said double-stranded nucleic acid is DNA.

26. The medical diagnostic process according to claim 15, wherein lower aliphatic alcohols are selected from the group consisting of methanol, ethanol, isopropanol, butanol, and pentanol, and said salts are selected from the group consisting of NaCl, KCl, LiCl, $MgCl_2$, and NaAc.

27. The medical diagnostic process according to claim 16, wherein lower aliphatic alcohols are selected from the group consisting of methanol, ethanol, isopropanol, butanol, and pentanol, and said salts are selected from the group consisting of NaCl, KCl, LiCl, $MgCl_2$, and NaAc.

28. The medical diagnostic process according to claim 17, wherein lower aliphatic alcohols are selected from the group consisting of methanol, ethanol, isopropanol, butanol, and pentanol, and said salts are selected from the group consisting of NaCl, KCl, LiCl, $MgCl_2$, and NaAc.

29. The medical diagnostic process according to claim 18, wherein lower aliphatic alcohols are selected from the group consisting of methanol, ethanol, isopropanol, butanol, and pentanol, and said salts are selected from the group consisting of NaCl, KCl, LiCl, $MgCl_2$, and NaAc.

30. The medical diagnostic process according to claim 20, wherein said biological source is selected from blood, plasma, serum, urine, feces, bacteria, viruses, mixtures obtained by (I) enzymatic in vitro transcription, cDNA synthesis, or reverse transcription followed by (ii) PCR synthesis.

* * * * *